United States Patent [19]

Nagaoka et al.

[11] Patent Number: 5,698,534
[45] Date of Patent: Dec. 16, 1997

[54] ANTIULCER AGENT AND PROCESS FOR PREPARING THE SAME

[75] Inventors: Masato Nagaoka; Shusuke Hashimoto; Tsunekazu Watanabe; Teruo Yokokura, all of Tokyo, Japan

[73] Assignee: Kabushiki Kaisha Yakult Honsha, Tokyo, Japan

[21] Appl. No.: 202,642

[22] Filed: Feb. 28, 1994

[30] Foreign Application Priority Data

Feb. 26, 1993 [JP] Japan ..................... 5-061447

[51] Int. Cl.⁶ .................. A61K 31/715; A61K 31/70
[52] U.S. Cl. ..................... 514/54; 514/60; 514/62
[58] Field of Search ................... 514/54, 60, 62

[56] References Cited

FOREIGN PATENT DOCUMENTS

A45236 1/1992 Japan.

OTHER PUBLICATIONS

Patent Abstract of Japan, vol. 12, No. 405 (C–539) Oct. 26, 1988 & JP–A–63 145 293 (Towa Kasei Kogyo K.K.) Jun. 17, 1988.
GB–A–2 056 856 (Kureha Kagaku Kogyo) Mar. 25, 1981.
JP–A–4 018 401 Tsumura & Co) Jan. 22, 1992.
JP–A–4 005 236 (Yakult Honsha KK) Jan. 9, 1992.
Yamada, H. et al, "Purification of Anti–Ulcer Polysaccharides from the Roots of *Buplerum Falcatum*", *Planta Medica*, vol. 57, No. 6, pp. 555–559, Dec. 1991.
Sun, X.B. et al., "Purification of an Anti–Ulcer Plysaccharide from the Leaves of *Panax Ginseng*", *Planta Medica*, vol. 58, No. 5, pp. 445–448, Oct. 1992.
JP–A–63 079 893 (Towa Kasei Kogyo K.K.) Apr. 1988 *abstract*.
JP–A–62 126 193 (Towa Kasei Kogyo K.K.) Jun. 1987 *abstract*.

Primary Examiner—Theodore J. Criares
Attorney, Agent, or Firm—Sughrue, Mion, Zinn, Macpeak & Seas, PLLC

[57] ABSTRACT

An antiulcer agent effective on prevention of ulceration and acceleration of healing of ulcers and processes for preparing the same are disclosed. The antiulcer agent comprises rhamnan (a homopolysaccharide), rhamnose or a rhamnose oligomer as an active ingredient. Rhamnan is prepared by separating rhamnan sulfate from rhamnan sulfate-containing algae and desulfurating the rhamnan sulfate. Rhamnan oligomers are prepared by hydrolyzing rhamnan obtained by desulfuration of rhamnan sulfate or by hydrolyzing microbial cells of a Bifidobacterium or polysaccharides separated therefrom.

7 Claims, No Drawings

ANTIULCER AGENT AND PROCESS FOR PREPARING THE SAME

FIELD OF THE INVENTION

This invention relates to an antiulcer agent effective for prevention and treatment of a gastric ulcer and to a process for preparing the same.

BACKGROUND OF THE INVENTION

Conventional antiulcer agents include those for controlling gastric juice secretion, such as $H_2$-blockers and proton pump inhibitors. Since a relapse of a gastric ulcer often appears after discontinuation of administration of these drugs, use of prostaglandins or gastric mucosa protecting agents has recently been studied.

On the other hand, the present inventors previously found that microbial cells of certain species of Bifidobacteria or lactic acid bacteria and polysaccharides extracted therefrom are effective in not only the prevention of ulceration but also in the acceleration of healing of ulcers and are useful as antiulcer agents (see JP-A-4-5236, the term "JP-A" as used herein means an "unexamined published Japanese patent application"). The polysaccharides of Bifidobacterium origin, whose antiulcer action had been confirmed, are heteropolysaccharides composed of rhamnose, glucose, galactose, glucosamine, etc. The mechanism of antiulcer action of the above-mentioned microbial cells or polysaccharides has not yet been elucidated.

SUMMARY OF THE INVENTION

An object of the present invention is to provide a novel antiulcer agent effective in the prevention of ulceration and in the acceleration of healing of ulcers.

Another object of the present invention is to provide a process for preparing the above-described antiulcer agent.

The present invention relates to an antiulcer agent containing rhamnan, which is a homopolysaccharide, as an active ingredient and to an antiulcer agent containing rhamnose or a rhamnose oligomer as an active ingredient.

The present invention also relates to (1) a process for preparing an antiulcer agent comprising separating rhamnan sulfate from rhamnan sulfate-containing algae, subjecting the rhamnan sulfate to desulfuration, recovering rhamnan from the reaction product, and using the resulting rhamnan as an active ingredient, (2) a process for preparing an antiulcer agent comprising separating rhamnan sulfate from rhamnan sulfate-containing algae, subjecting the rhamnan sulfate to desulfuration, hydrolyzing the resulting rhamnan, recovering rhamnan having a reduced molecular weight and/or rhamnose oligomers from the hydrolysis product, and using the resulting rhamnan having a reduced molecular weight and/or rhamnose oligomers as an active ingredient, or (3) a process for preparing an antiulcer agent comprising subjecting microbial cells of a Bifidobacterium or polysaccharides separated therefrom to hydrolysis, recovering rhamnan, which is a homopolysaccharide, and/or rhamnose oligomers from the hydrolysis product, and using them as an active ingredient.

DETAILED DESCRIPTION OF THE INVENTION

In the present invention, homopolysaccharides composed of 7 or more molecules of rhamnose are designated "rhamnan", and those composed of 2 to 6 molecules of rhamnose, while included in the terminology "polysaccharides" in its broad sense but markedly differing from rhamnan in solubility, taste, and chemical properties, are designated "rhamnose oligomers" in distinction from "rhamnan".

Rhamnan which is a homopolysaccharide, rhamnose, and a rhamnose oligomer exhibit antiulcer activity no less potential than that of the above-described heteropolysaccharides of Bifidobacterium origin.

The antiulcer agent according to the present invention is orally administered and seems to reach the affected part through the digestive tract to exercise a healing action, while the mechanism of the action has not yet been made clear.

The antiulcer agent comprising rhamnan as an active ingredient can be prepared advantageously by process (1) which has been stated above and will be described below in detail.

Rhamnan sulfate is recovered from algae containing rhamnan sulfate. Usable rhamnan sulfate-containing algae include green laver (*Monostroma nitidum*). Rhamnan sulfate can be separated from the algae by, for example, the following steps. Dry algae are suspended in water, and the suspension is heated to exude rhamnan sulfate. Solids are removed by centrifugal separation, and ethanol is added to the supernatant to precipitate polysaccharides, which are collected and dissolved in water. The solution is subjected to dialysis to obtain a dialyzate containing rhamnan sulfate and free from low-molecular weight components.

Hydrochloric acid or sodium hydroxide is added to the rhamnan sulfate-containing dialyzate, followed by heating to about 100° C. to induce desulfuration. The reaction system is again subjected to dialysis to obtain rhamnan as a dialyzate.

Desulfuration of rhamnan sulfate may also be performed by solvolysis. For the detail, *ZOKU-SEIKAGAKU JIKKEN KOZA 4•FUKUGO TANPAKU KENKYUHO II* (Sequel Biochemical Experiment Lecture 4•Heteropolysaccharides Research II, Tokyo Kagaku Dojin). In this case, rhamnan sulfate is heated in water or dimethyl sulfoxide containing about 10% methanol to cause desulfuration. A non-solvent, such as ethanol, is added thereto to precipitate rhamnan, which is then collected and subjected to dialysis to obtain rhamnan free from impurities.

In using the rhamnan resulting from desulfuration of rhamnan sulfate as an antiulcer agent, the desulfuration is desirably conducted completely, but it is practically acceptable that the rhamnan may contain residual bound sulfuric acid.

The antiulcer agent comprising a rhamnose oligomer as an active ingredient is prepared by process (2) or (3) which has been described above and will be described below in detail. Where process (2) is followed, rhamnan prepared by process (1) is decomposed by acid hydrolysis or periodic acid oxidation to obtain rhamnose oligomers. If the degree of decomposition rhamnan undergoes is insufficient so that the resulting decomposition product has a reduced molecular weight but is still regarded as rhamnan, such a product is also useful as an active ingredient of the antiulcer agent of the present invention.

Where process (3) is followed, a rhamnose oligomer is obtained from a Bifidobacterium containing rhamnan as a cell wall component. In this case, a Bifidobacterium is cultured in an arbitrary culturing method. Examples of usable Bifidobacteria include *B. breve*, *B. bifidum*, *B. adolescentis*, *B. catenulatum*, *B. longum*, etc. Among them, *B. breve* YIT 4008 (FERM BP-4538) is preferred because most of the polysaccharides obtained therefrom are monopolysaccharides.

*B. breve* YIT 4008 is deposited at National Institute of Bioscience and Human-Technology Agency of Industrial Science and Technology whose address is 1–3, Higashi 1-chome, Tsukuba-shi, Ibaraki 305 Japan on Feb. 19, 1993 as an accession number of FERM BP-4538.

Culturing can be carried out in a known liquid medium for Bifidobacteria, such as Rogosa's medium described in the JFCC catalogue, under arbitrarily selected conditions.

After completion of the culture, the microbial cells are collected from the culture in a usual manner, for example, by centrifugation, and washed with distilled water until the medium components disappear to obtain clean microbial cells.

Polysaccharides constituting the microbial cells are then extracted from the microbial cells in an arbitrary manner. For instance, the cells are suspended in an isotonic solution and treated with a cell wall lytic enzyme,. e.g., N-acetylmuramidase. Prior to the enzymatic treatment, the cells may be ruptured by ultrasonification or by means of a French press. After the enzymatic treatment, solid cytoplasm is removed from the cell suspension by centrifugation, and the supernatant liquor is treated with a nuclease and subsequently with trypsin or pronase to decompose the protein. Finally, the decomposition system is dialyzed against distilled water to remove low-molecular weight fractions and lyophilized.

The resulting polysaccharides are hydrolyzed with an acid (e.g., dilute hydrochloric acid, dilute sulfuric acid or trifluoroacetic acid) or an enzyme to recover rhamnose oligomers.

It is possible to subject the microbial cells of a Bifidobacterium directly to hydrolysis to effect extraction of polysaccharides in parallel to hydrolysis. This process is advantageous in the case where the intended rhamnose oligomers do not need to be highly pure.

Depending on the conditions of the above-mentioned treatments, cases may arise in which the whole or part of the cell constituting rhamnan is not cleaved into low-molecular weight "oligomers" and the system remains with "rhamnan" having a relatively low molecular weight. Such rhamnan having a reduced molecular weight or a rhamnose oligomer mixture therewith also serves as an active ingredient of the antiulcer agent of the present invention.

Because the antiulcer agent of the present invention comprises sugars or polysaccharides obtained from edible algae or Bifidobacteria which have been in long use for manufacture of dairy products, it is of high safety. Therefore, the preparation form and the dose can be selected arbitrarily. In general, the active ingredient is compounded with pharmaceutically acceptable liquid or solid carriers and, if desired, with adjuvants, such as a solvent, a dispersant, an emulsifying agent, a buffering agent, a stabilizer, a vehicle, a binder, a disintegrator, a lubricant, and so forth, and formulated into tablets, granules, dusts, powders, capsules, and the like.

The antiulcer agent according to the present invention can be administered orally or may be added to foods and drinks for daily intake.

While not limiting, a suitable dose of the antiulcer agent ranges from about 1 to 500 mg/kg, and preferably from 5 to 50 mg/kg, per day for adults.

The present invention will now be illustrated in greater detail with reference to Examples and a Test Example, but it should be understood that the present invention be not construed as being limited thereto.

EXAMPLE 1

In 0.01N trifluoroacetic acid was suspended 50 mg/ml of lyophilized cells of *Bifidobacterium breve* YIT 4008 which had been cultured in a modified Rogosa's medium. The cell suspension was heated at 100° C. for 15 minutes, followed by centrifugation to remove solids. The supernatant liquor was concentrated to dryness. The residue was dissolved in water, and the solution was desalted by dialysis. The dialyzate was subjected to ultrafiltration using a membrane having a molecular weight separation limit of 50000.

The ultrafiltrate contained polysaccharides mainly comprising rhamnan, a monosaccharide, having a relatively low molecular weight.

EXAMPLE 2

Dried green laver (*Monostroma nitidum*) was suspended in 10 times the volume of water, and the suspension was heated at 100° C. for 2 hours to exude rhamnan sulfate. Solids were separated by centrifugation, and ethanol was added to the supernatant liquor. The thus precipitated polysaccharides were collected, dissolved in water, and subjected to dialysis to remove low-molecular weight components. To the dialyzate containing rhamnan sulfate was added hydrochloric acid to a normality of about 0.01, and the mixture was heated to 100° C. to effect desulfuration. The reaction mixture was again dialyzed to obtain a rhamnan-containing dialyzate.

EXAMPLE 3

Rhamnan sulfate was recovered from green laver in the same manner as in Example 2 and heated in dimethyl sulfoxide containing 10% methanol to cause desulfuration. Ethanol was added to the reaction mixture to precipitate rhamnan. The precipitate was collected and dialyzed to obtain an impurity-free rhamnan-containing dialyzate.

EXAMPLE 4

The rhamnan prepared in Example 2 was hydrolyzed with an acid, and the reaction mixture was subjected to gel filtration and then fractionated by column chromatography on activated carbon to obtain rhamnose oligomers.

TEST EXAMPLE

The rhamnan and rhamnose oligomers prepared in Examples 1 to 4 and commercially available rhamnose were tested for antiulcer activity on acetic acid-induced ulceration.

Laparotomy was performed on ten 8-week-old SD rats (body weight: 250–300 g) per group under anesthesia with Nembutal. The stomach was exposed, and 0.03 ml of 20% acetic acid was injected in the submucous coat of the corpus ventriculi to induce ulceration. The test substance was orally given to the animals at a daily dose shown in Tables 1 to 5 below from the 2nd to 9th days from the operation. During the testing period, the animals were fed on food and water, ad lib. On the 10th day, the stomach was excised, and the area of the ulcerated part (longer diameter×shorter diameter) was measured as an ulceration index. A percent healing was calculated from the ulceration index according to equation:

Percent healing (%)=(1−Ulceration index of test group/Ulceration index of control group)×100

The results obtained are shown in Tables 1 to 5. The ulceration indices in the Tables are expressed as mean±standard deviation.

TABLE 1

Antiulcer Effect of Rhamnan of Example 1

| Dose (mg/rat) | Ulceration Index | Percent Healing (%) |
|---|---|---|
| 0 (control) | 12.0 ± 4.6 | — |
| 0.75 | 10.1 ± 2.5 | 15.4 |
| 1.50 | 5.7 ± 2.8* | 52.2 |
| 3.00 | 5.2 ± 4.0* | 56.5 |

Note: *Significant at an error of 5% or less

TABLE 2

Antiulcer Effect of Rhamnan of Example 2

| Dose (mg/rat) | Ulceration Index | Percent Healing (%) |
|---|---|---|
| 0 (control) | 12.4 ± 4.7 | — |
| 1.50 | 10.0 ± 5.0 | 19.4 |
| 3.00 | 9.6 ± 3.9 | 22.5 |
| 6.00 | 6.2 ± 3.1* | 50.3 |

Note: *Significant at an error of 5% or less

TABLE 3

Antiulcer Effect of Rhamnan of Example 3

| Dose (mg/rat) | Ulceration Index | Percent Healing (%) |
|---|---|---|
| 0 (control) | 8.2 ± 2.6 | — |
| 1.50 | 5.2 ± 2.6* | 37.0 |
| 3.00 | 6.1 ± 3.1 | 25.7 |
| 6.00 | 5.1 ± 1.4* | 38.3 |

Note: *Significant at an error of 5% or less

TABLE 4

Antiulcer Effect of Rhamnose Oligomers of Example 4

| Dose (mg/rat) | Ulceration Index | Percent Healing (%) |
|---|---|---|
| 0 (control) | 10.3 ± 6.2 | — |
| 1.50 | 7.6 ± 3.4 | 26.1 |
| 3.00 | 5.6 ± 2.8* | 46.1 |
| 6.00 | 6.5 ± 3.4 | 37.4 |

Note: *Significant at an error of 5% or less

TABLE 5

Antiulcer Effect of Rhamnose Monosaccharide (manufactured by SIGMA CHEMICAL COMPANY)

| Dose (mg/rat) | Ulceration Index | Percent Healing (%) |
|---|---|---|
| 0 (control) | 12.6 ± 2.0 | — |
| 7.50 | 6.6 ± 2.7* | 47.1 |
| 15.00 | 6.0 ± 2.2* | 52.1 |
| 30.00 | 9.7 ± 5.0 | 22.9 |

Note: *Significant at an error of 5% or less

As described and demonstrated above, the present invention provides an antiulcer agent which exhibits excellent ulcer healing accelerating activity and high safety and which can be prepared with ease.

While the invention has been described in detail and with reference to specific examples thereof, it will be apparent to one skilled in the art that various changes and modifications can be made therein without departing from the spirit and scope thereof.

What is claimed is:

1. A process for treating a person in need of ulcer treatment or ulcer prevention, consisting of the step of administering to that person an antiulcer agent consisting of rhamnan, rhamnose, or rhamnose oligomer.

2. The process as claimed in claim 1, wherein said rhamnan is derived from *Bifidobacterium breve* YIT 4008 (FERM BP-4538).

3. The process as claimed in claim 1, wherein said rhamnose or rhamnose oligomer is derived from *Bifidobacterium breve* YIT 4008 (FERM BP-4238).

4. The process as claimed in claim 1, wherein the rhamnan is prepared by a process comprising separating rhamnan sulfate from rhamnan sulfate-containing algae, subjecting the rhamnan sulfate to desulfuration, and recovering said rhamnan from the reaction product.

5. The process as claimed in claim 1, wherein the antiulcer agent consists of, as an active ingredient, rhamnan having a reduced molecular weight and/or rhamnose oligomers, wherein the active ingredient is prepared by a process comprising separating rhamnan sulfate from rhamnan sulfate-containing algae, subjecting the rhamnan sulfate to desulfuration, hydrolyzing the resulting rhamnan, and recovering said rhamnan having a reduced molecular weight and/or said rhamnose oligomers from the hydrolysis product.

6. The process as claimed in claim 1, wherein the antiulcer agent consists of rhamnan as an active ingredient.

7. The process as claimed in claim 1, wherein the antiulcer agent consists of rhamnose or a rhamnose oligomer as an active ingredient.

* * * * *